United States Patent [19]

Tawara

[11] 4,318,395
[45] Mar. 9, 1982

[54] ENDOSCOPE OCULAR ACCESSORY MOUNTING DEVICE

[75] Inventor: Ikuo Tawara, Hachioji, Japan

[73] Assignee: Olympus Optical Co., Ltd., Tokyo, Japan

[21] Appl. No.: 149,855

[22] Filed: May 14, 1980

[30] Foreign Application Priority Data

May 23, 1979 [JP] Japan .................................. 54-69289

[51] Int. Cl.³ .......................... A61B 1/00; G03B 17/00
[52] U.S. Cl. .......................................... 128/4; 354/62; 403/322; 350/257
[58] Field of Search ...................... 128/4, 6, 8; 354/62, 354/79, 286, 295, 296; 403/316, 318, DIG. 4, 322; 350/257

[56] References Cited

U.S. PATENT DOCUMENTS 3,922,011 11/1975 Walters ................................ 285/277
4,066,330 1/1978 Jones ................................ 403/322 X
4,182,558 1/1980 Matsuo ............................ 354/62 X

FOREIGN PATENT DOCUMENTS 2757358 1/1980 Fed. Rep. of Germany .

Primary Examiner—Stephen C. Pellegrino

Attorney, Agent, or Firm—Frishauf, Holtz, Goodman and Woodward

[57] ABSTRACT

An endoscope ocular accessory mounting device comprises a mounting body provided at its forward end with a flanged section having a truncated conical cavity for mounting an ocular accessory on an endoscope ocular section. A pair of axially extending slits are formed in the peripheral wall diametrically facing each other across the circular flanged section. A cam plate is swingably fitted into each of the slits. This cam plate is so urged that its inner end cam surface is engaged with the truncated conical rear part of the endoscope ocular section. A pair of push rods penetrate the peripheral wall of a ring member surrounding the flanged section. Each push rod is urged radially to the outside of the ring member and provided with a release button at the outer end. Where the paired push rods are pushed, the inner end of each push rod pushes the outer end cam surface of the cam plate, causing the cam plate to be rotated out of a passage formed in the endoscope ocular section, and consequently enabling the mounting device to be released from the endoscope ocular section. The endoscope ocular accessory mounting device has a simple arrangement and can be operated quickly, easily and unfailingly substantially without failure and manufactured at low cost.

6 Claims, 3 Drawing Figures

ENDOSCOPE OCULAR ACCESSORY MOUNTING DEVICE

BACKGROUND OF THE INVENTION

This invention relates to an endoscope ocular accessory mounting device which detachably mounts an endoscope ocular accessory including a camera and teaching scope (or auxiliary scope) on the ocular section of an endoscope.

Where the interior of a coeliac cavity taken as an object of observation is surveyed by a plurality of persons at the same time or is photographed, a teaching scope or teaching scopes or a camera is mounted on the ocular section of an endoscope by an ocular accessory mounting.

The attachment of the above-mentioned accessory to the ocular section of the endoscope or the detachment of the accessory therefrom is carried out while the endoscope is inserted into the coeliac cavity and moreover often immediately before or after the affected part of the coeliac cavity undergoes a small scale medical operation. Therefore, the above-mentioned attachment and detachment of the accessory should of course be carried out easily an quickly and with great safety in order to protect the coeliac cavity of a patient from danger resulting from an unnecessary load imposed on the cavity.

The known endoscope ocular accessory mounting devices include the type which comprises a bayonet, and the type which utilizes a frictional force occurring between the accessory and endoscope ocular section. However, these conventional accessory mounting devices have the drawbacks that the devices have a complicated arrangement; the accessory cannot be attached to or detached from the endoscope ocular section by a single hand; and the removal of the accessory from the ocular section needs the application of a great force, causing the endoscope as a whole to be unnecessarily shaken and consequently imparting pains or injuries to the interior of a patient's coeliac cavity. Particularly where the accessory mounting device has a complicated arrangement, the attachment and detachment of the device involves a troublesome procedure, unavoidably resulting in the occurrence of the failure of an endoscope as a whole or its high cost.

SUMMARY OF THE INVENTION

It is accordingly the object of this invention to provide an inexpensive endoscope ocular accessory mounting device of simple arrangement which can be attached to or detached from the endoscope ocular section quickly, easily and unfailingly and is moreover little subject to failure.

An ocular accessory mounting device embodying this invention comprises a mounting body provided with a flanged section having a truncated conical mounting cavity for receiving an endoscope ocular section, said mounting cavity having its diameter progressively reduced inward. The outer wall of the flanged section is provided with a slit extending axially of the mounting cavity, or a pair of slits which diametrically face each other right across the mounting cavity and extend likewise axially of the mounting cavity. A cam plate having inner and outer cam surfaces is rotatably fitted into the slit or slits by a pivotal shaft. The inner end cam surface of the cam plate is always urged by an elastic urging means to be rotated toward the open end of the mounting cavity. The inner end cam surface has a segmental shape whose center is positioned more inward of the mounting cavity than the above-mentioned pivotal shaft.

A ring member surrounding the flanged section is fixed at one end to a mounting body. That portion of the lateral wall of the ring member which is disposed nearer to the open end of the mounting cavity than the pivotal shaft is penetrated by a push rod whose inner end is engageable with the outer end cam surface of the cam plate. The push rod is always urged by an elastic urging means to project radially to the outside of the mounting cavity. When pushed at the outer end with the finger, the push rod is forced into the mounting cavity.

Where a mounting device is to be fitted to the endoscope ocular section, the mounting device has only to be forced in with the endoscope ocular section and the mounting cavity of the mounting body substantially aligned with each other. Once set in this state, the mounting device does not come off the endoscope ocular section even when pulled later. The removal of the mounting device from the ocular section is effected by the steps of pushing the outer end of the push rod with a finger to force the push rod into the mounting cavity, causing the inner end of the push rod to push the outer end cam surface of the cam plate which faces the inner end of the push rod, and rotating the cam plate to the outside of the passage of the ocular section against the force of the elastic urging means. Since the above-mentioned steps prevent the cam plate from striking against the ocular section, the mounting device can be easily released from the ocular section.

The mounting device simply constructed as described above has the advantages that it can be easily operated substantially without failure, manufactured at low cost, and moreover fitted to and removed from the endoscope ocular section quickly, easily and unfailingly.

BRIEF DESCRIPTION OF THE DRAWING

This invention can be fully understood from the following detailed description with reference to the accompanying drawings in which.

DETAILED DESCRIPTION OF THE PREFERRED EMBODIMENT

Figure 1:
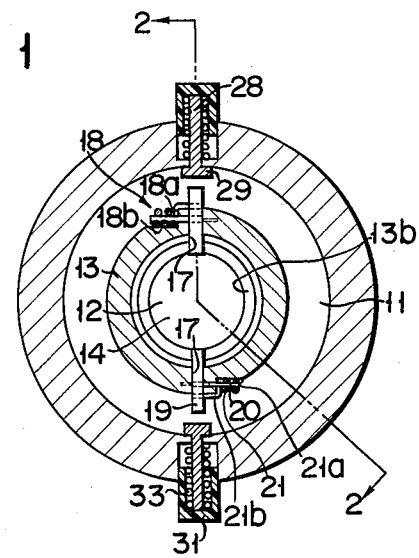
FIG. 1 is a cross sectional view of a device for mounting an accessory of an endoscope ocular on an endoscope ocular embodying this invention.

A cylindrical member designated by reference numeral 11 throughout the drawing is a mounting body integrally formed with or detachably connected to an endoscope ocular accessory including a camera and teaching scope (or an auxiliary scope). This mounting body 11 is provided at the center with a hole 12 concentrically extending with the axis of an optical system of the endoscope ocular accessory.

A cylindrical flanged section 13 is integrally formed with the mounting body 11 at one end. A truncated conical mounting cavity 14 of an endoscope ocular section 15 is defined in the flanged section 13 concentrically with the central hole 12. The diameter of the mounting cavity 14 progressively increases toward the free end or outer end 13a of the cavity 14 (namely, progressively decreases toward the inner end 13b). The inner end 13b of the mounting cavity 14 has a diameter substantially equal to the outer diameter of the endoscope ocular section 15. The central hole 12 has a smaller diameter than that of the inner end 13b of the mounting cavity 14. Thus, the central hole 12 and mounting cavity 14 collectively define an annular stepped portion 16. Where, therefore, the endoscope ocular section 15 is pushed to the deepest part of the mounting cavity 14, the front end face 15a of the endoscope ocular section 15 abuts against the stepped portion 16, thereby fixing the axial position of the endoscope ocular section 15. At this time, the lateral wall 15b of the endoscope ocular section 15 is tightly engaged with the inner end 13b of the mounting cavity 14, thereby preventing the endoscope ocular section 15 from being displaced crosswise. As shown in FIG. 1, a pair of elongated slits 17 are formed in the lateral wall of the flanged section 13. The slits 17 extend axially of the mounting cavity 14 and diametrically face each other across the circular lateral wall of the flanged section 13. As seen from FIG. 1, notches 18 are respectively formed closely to the slits 17 in the outer peripheral wall of the flanged section 13. Each of the notches 18 has a plane 18a parallel with the slit 17 and a plane 18b perpendicular to the slit 17.

A cam plate 19 is fitted into the slit 17. The central portion of the cam plate 19 is inserted into the flanged section 13. The cam plate 19 is penetrated by a shaft 20 fixed to the flanged section 13, thereby being rendered swingable about the shaft 20.

A torsion spring 21 is wound about that portion of the shaft 20 which projects outward from the plane 18a of the notch 18. One arm 21a of the torsion spring 21 presses the plane 18b of the notch 18 formed in the flanged section 13. The other arm 21b of the torsion spring 21 is anchored on a shoulder 22 formed at an intermediate portion of that side of the cam plate 19 which faces the inner end 13b of the mounting cavity 14. As a result, the inner end cam surface 23 is always elastically urged to be moved apart from the inner end 13b of the mounting cavity 14.

Figure 2:
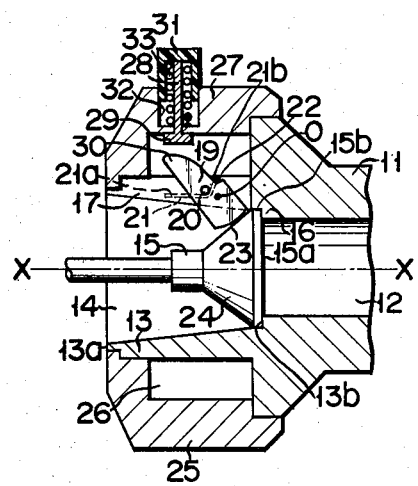
FIG. 2 is a cross sectional view of FIG. 1 along line 2—2.

As shown in FIG. 2, the inner end cam surface 23 has a segmental shape whose center 0 is situated closer to the inner end 13b of the mounting cavity 14 than the shaft 20. The inner end cam surface 23 touches the peripheral wall of the truncated conical rear part 24 of the endoscope ocular section 15 inserted into the mounting cavity 14. As a result, the front end face 15a of the endoscope ocular section 15 is pressed against the stepped portion 16 by the urging force of the torsion spring 21. Where, under the condition of FIG. 2, an attempt is made to pull the mounting device from the endoscope ocular section 15, the inner end cam surface 23 of the cam plate 19 acts as if to bite into the rear part 24 of the endoscope ocular section 15, thereby ensuring that the accessory is prevented from falling off the endoscope ocular section 15 by any chance during the operation of an endoscope.

The flanged section 13 is surrounded by a ring member 25 having a hollow cylindrical space 26. Both ends of the ring member 25 are respectively fixed to the outer end 13a of the flanged section 13 and the outer end of the mounting body 11. A push rod 28 radially penetrates that portion of the peripheral wall 27 of the ring member 25 which lies closer to the outer end 13a of the mounting cavity 14 than the shaft 20. The inner end 29 of the push rod 28 has its diameter made larger than any other part thereof to be unfailingly engaged with the outer cam surface 30 of the cam plate 19. The outer end cam surface 30 constitutes a segmental plane formed on that side of the cam plate 19 which faces the inner end 13b of the flanged section 13. A release button 31 having a U-shaped cross section is fixed to the outer end of the push rod 28. The skirt of the release button 31 is inserted into a radially extending blind ended hole 32 formed in the peripheral wall 27 of the ring member 25. A compression coil spring 33 surrounding the push rod 28 extends between the bottom of the hole 32 and push button 31. The compression coil spring 33 urges both the push rod 28 and push button 31 radially to the outside of the ring member 25.

In operation, the outer end cam surface 30 of the cam plate 19 is pressed against the inner end 29 of the push rod 28 by the torsion coil spring 21, when the mounting device is not fitted to the endoscope ocular section 15, or when the push button 31 is not pressed.

Where, under the above-mentioned condition, the mounting device is pushed in with the axis X—X of the mounting cavity 14 substantially aligned with the optical axis of the endoscope ocular section 15, the cam plate 19 is rotated by the front end face 15a of the endoscope ocular section 15 against the urging force of the torsion coil spring 21, and rides over the lateral wall 15b of the endoscope ocular section 15, and thereafter the inner end cam surface 23 of the cam plate 19 is engaged with the peripheral wall of the rear part 24 of the endoscope ocular section 15. The torsion coil spring 21 causes the inner end cam surface 23 of the cam plate 19 to push the rear part 24 of the endoscope ocular section 15, so that the endoscope ocular section 15 is pushed toward the central hole 12. As a result, the front end face 15a of the endoscope ocular section 15 abuts against the stepped portion 16. Therefore, the mounting device is prevented from being moved either axially or radially of the endoscope ocular section 15. Where, therefore, an attempt is made to pull out the mounting device set in the above-mentioned state, the mounting device obviously does not fall off the endoscope ocular section 15, as previously described.

The mounting device is released from the endoscope ocular section 15 by the following steps.

Figure 3:
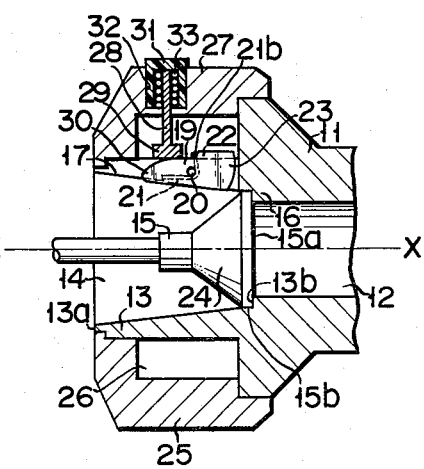
FIG. 3 is a cross sectional view of FIG. 1 along line 2—2, in which a release button is depressed to rotate a plate cam out of the passage of an endoscope ocular fitted in the mounting cavity formed in the mounting device.

A pair of push buttons 31 (FIG. 1) are pushed with the finger from the state indicated in FIG. 2 to the state shown in FIG. 3. Then the push rod 28 is moved radially into the ring member 25. As a result, the inner end 29 of the push rod 28 pushes the outer end cam surface 30 of the cam plate 19. Therefore, the cam plate 19 is rotated, as shown in FIG. 3, against the urging force of the torsion coil spring 21 to be situated outside of the passage of the endoscope ocular section 15. Where the mounting device is pulled along the optical axis of the endoscope ocular section 15 with the push buttons 31 depressed, the mounting device is removed from the endoscope ocular section 15 easily and unfailingly. Where the finger is released from the push buttons after the removal of the mounting device, the mounting device is brought back to the position occupied by the device before being fitted to the endoscope ocular section 15.

The foregoing embodiment comprises a pair of cam plates, push rods and release buttons. However, only one set of a cam plate, push rod and release button may be used.

What is claimed is:

1. An endoscope ocular accessory mounting device comprising:
    a mounting body having a central hole and one end;
    a flanged section which is formed at said one end of the mounting body and in which a truncated conical cavity for receiving an endoscope ocular section is formed, said cavity having a diameter progressively reduced toward said mounting body and being formed concentrically with said central hole;
    an enlongated slit formed in the flanged section in a state extending axially thereof;
    a cam plate which is fitted into said elongated slit in a state swingable about a shaft provided in said elongated slit, and having an inner end cam surface assuming a segmental shape whose center lies closer to the mounting body than said shaft and an outer end cam surface formed on the opposite side of said cam plate to said shaft, and said cam plate being provided with an elastic urging means for urging the cam plate to cause said inner end cam surface to be rotated about said shaft toward the mounting body;
    a ring member surrounding said flanged section and fixed to said mounting body; and
    a cam plate releasing means which pushes the outer end cam surface of the cam plate to rotate said cam plate against an urging force of said elastic urging means, for releasing said cam plate from the endoscope ocular section received in the mounting cavity, said cam plate releasing means comprising a push rod which reciprocably penetrates the ring member at a portion of the ring member which is on the side of said shaft which is opposite the mounting body, an inner end of the push rod being interior of the ring member and being selectively engageable with the outer end cam surface of the cam plate and an outer end of the push rod projecting radially out of the ring member, and an elastic urging member provided in the ring member to elastically urge the push rod radially outward of the ring member.

2. The endoscope ocular accessory mounting device according to claim 1, which further comprises:
    another elongated slit formed in the flanged section to diametrically face the aforesaid elongated slit across said circular flanged section;
    another cam plate which is fitted into said another elongated slit in a state swingable about another shaft provided in said another elongated slit, whose inner end cam surface assumes a segmental shape having a center disposed closer to the mounting body than said another shaft and whose outer end cam surface is formed on the opposite side of said cam plate to said another shaft; and
    another elastic urging means for urging said another cam plate to cause the inner end cam surface to be rotated about said another shaft toward the mounting body;
    another cam plate releasing means comprising another push rod which reciprocably penetrates the ring member at a portion of the ring member which is on the side of said another shaft which is opposite the mounting body, and whose inner end is engageable with the outer end cam surface of said another cam plate and whose outer end projects radially out of the ring member, and another elastic urging member which is provided in the ring member to urge said another push rod radially outward of said ring member.

3. The endoscope ocular accessory mounting device according to claim 1 or 2, wherein the inner end of the push rod has a diameter made larger than any other part of said push rod.

4. The endoscope ocular accessory mounting device according to claim 3, wherein the outer end of the push rod is fitted with a release button.

5. The endoscope ocular accessory mounting device according to claim 4, wherein the cam plate releasing means includes a bottomed hole formed in the ring member to surround the push rod; and the elastic urging member comprises a compression coil spring surrounding the push rod in the bottomed hole.

6. The endoscope ocular accessory mounting device according to claim 1 or 2, wherein said flanged section is integrally formed with said mounting body.

* * * * *